(12) United States Patent
Sinha et al.

(10) Patent No.: US 8,779,200 B2
(45) Date of Patent: Jul. 15, 2014

(54) MICROWAVE INDUCED SINGLE STEP GREEN SYNTHESIS OF SOME NOVEL 2-ARYL ALDEHYDES AND THEIR ANALOGUES

(75) Inventors: Arun Kumar Sinha, Himachal Pradesh (IN); Abhishek Sharma, Himachal Pradesh (IN); Rakesh Kumar, Himachal Pradesh (IN); Naina Sharma, Himachal Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 56 days.

(21) Appl. No.: 13/203,100

(22) PCT Filed: Feb. 25, 2010

(86) PCT No.: PCT/IN2010/000110
§ 371 (c)(1),
(2), (4) Date: Oct. 28, 2011

(87) PCT Pub. No.: WO2010/097811
PCT Pub. Date: Sep. 2, 2010

(65) Prior Publication Data
US 2012/0041234 A1 Feb. 16, 2012

(30) Foreign Application Priority Data
Feb. 25, 2009 (IN) .............................. 348/DEL/2009

(51) Int. Cl.
*C07C 241/00* (2006.01)
*C07C 47/00* (2006.01)

(52) U.S. Cl.
USPC .......................................... 564/251; 568/442

(58) Field of Classification Search
USPC ....................................................... 564/251
See application file for complete search history.

(56) References Cited

U.S. PATENT DOCUMENTS

| | | |
|---|---|---|
| 3,227,779 A | 1/1966 | Hopff et al. |
| 3,658,858 A | 4/1972 | Harrison |
| 3,658,863 A | 4/1972 | Harrison |
| 3,663,584 A | 5/1972 | Alvarez |
| 3,694,476 A | 9/1972 | Alvarez |
| 3,959,364 A | 5/1976 | Armitage et al. |
| 3,974,202 A | 8/1976 | El-Chahawi et al. |
| 4,536,595 A | 8/1985 | Gardano et al. |
| 4,601,797 A | 7/1986 | Wagenknecht |
| 4,713,484 A | 12/1987 | Epstein |
| 6,943,194 B1 | 9/2005 | Pettit et al. |
| 2002/0161266 A1 | 10/2002 | Larhed et al. |

FOREIGN PATENT DOCUMENTS

| | | |
|---|---|---|
| DE | 2145650 A1 | 3/1973 |
| EP | 0034871 A2 | 9/1981 |
| EP | 0076721 A1 | 4/1983 |
| EP | 0076722 A1 | 4/1983 |
| JP | 55-027147 A | 2/1980 |
| JP | 60-100536 A | 6/1985 |
| JP | 60-103193 A | 6/1985 |
| WO | 93/03839 A1 | 3/1993 |

OTHER PUBLICATIONS

Branytska, O; Shimon, LJW; and Neumann, R., Chem. Commun. (Cambridge UK) (2007), (38), 3957-3959.*
D.R. Arnold, et al; "Radical Ions in Photochemistry. 3. Photosensitized (Electron Transfer) Cleavage of β-Phenethyl Ethers[1]", Journal of The American Chemical Society, vol. 98, No. 19, Jan. 1, 1976, pp. 5931-5937, XP002589029; p. 5932, first column, paragraph 3 and the scheme in col. 1.
P. Lakshminarasimhan, et al; "Wavelength Dependent Oxygen Mediated Electron-Transfer Reactions within M+Zeolites: Photo Oxidation and Reduction of 1,1-Diarylethylenes", Langmuir, vol. 16, Oct. 31, 2000, pp. 9360-0367, XP002589030 Schemes 1 and 2.
Ronald L. Halterman, et al; "Diastereoselectivity in the Reduction of Sterically Unbiased 2,2-Diarylcyclopentanones", Journal of The American Chemical Society, vol. 112, Jan. 1, 1990, pp. 6690-6695, XP002589031, scheme I, Compound 5b.
Haruhiko Kikuchi, et al; "A Facile Preparation of 2-Arylpropionaldehyde From 1-Aryl-1-Propene", Chemistry Letters, Jan. 1, 1984, pp. 341-344, XP002589032 cited in the application the whole document.
International Search Report: mailed Jul. 16, 2010; PCT/IN2010/000110.

* cited by examiner

*Primary Examiner* — Wu-Cheng Winston Shen
*Assistant Examiner* — Kofi Adzamli
(74) *Attorney, Agent, or Firm* — Ladas & Parry LLP

(57) ABSTRACT

The present invention provides a process for the preparation of some novel 2-aryl and 2,2-diaryl aldehydes and analogues which are privileged intermediates for commercially important nonsteroidal anti-inflammatory drugs including naproxen, flurbiprofen and potent anticancer drug candidates, including phenstatin through a unique single step synthetic methodology utilizing easily available substrates in the form of aryl alkenes as well as environmentally benign aqueous reaction conditions in the form of solvents such as mixtures of water and DMSO or Dioxane and reagents N-bromosuccinimide, N-iodosuccinimide, N-cholorosuccinimide and phase transfer catalyst such as cetyltrimethyl ammonium bromide, N-hexyl ammonium chloride for a reaction time varying from 1 min-30 min, depending upon microwave or conventional heating, without using expensive transition metal catalysts or lewis acids/bases with yield varying from 35-55%, depending upon the solvent and substrate used. The developed method provides a clean and convenient alternative to access a diverse range of medicinally important 2-aryl and 2,2-diaryl aldehyde based scaffolds in lieu of the conventional multistep protocols employing expensive and hazardous transition metal catalysts and lewis acids/bases.

1 Claim, 3 Drawing Sheets

MICROWAVE INDUCED SINGLE STEP GREEN SYNTHESIS OF SOME NOVEL 2-ARYL ALDEHYDES AND THEIR ANALOGUES

FIELD OF INVENTION

The present invention relates to some novel 2-aryl and 2,2-diaryl aldehydes and analogues which are privileged intermediates for commercially important nonsteroidal anti-inflammatory drugs including naproxen, flurbiprofen and potent anticancer drug candidates including hydroxy phenstatin are synthesized through a novel microwave induced process which not only provides the highly valuable 2-aryl and 2,2-diaryl aldehydes from the corresponding aryl alkenes in a single step but also simultaneously eliminates the hitherto indispensable requirement of expensive and hazardous transition metal catalysts.

BACKGROUND ART

The 2-aryl aldehyde constitutes an immensely important synthon for the synthesis of various commercially and pharmacologically valuable compounds. For instance, the commercially important non steroidal anti-inflammatory drugs like naproxen (2-(6'-methoxy-2'-naphthyl)-propionic acid) and ibupfren (2-(4'-isobutylphenyl)-propionic acid) are alpha aryl alkanoic acids and their analogues which are synthesized through various synthetic approaches including the oxidation of corresponding 2-aryl aldehydes (C. Commun. 2007, 1739-1741; J. Org. Chem. 1999, 64, 5029-5035, Organometallics 10, 1183-1189, 1991, 1183, WO 9303839). In particular, naproxen has been widely recognized as an ace anti-inflammatory agent and ranked fourth in sales in the global pharmaceutical market in 1991. Similarly ibupfren is a well known anti-inflammatory drug which has been converted from ethical (prescription) to the counter status. Besides their synthesis using 2-aryl aldehydes as intermediates, the above 2-aryl alkanoic acids have also been synthesized from various other approaches, principal amongst them being the carbonylation of respective arylethyl alcohols (Japanese Kokai patent No SHO 55 (1980)-27147), electrocarboxylation of corresponding aryl methyl ketones (U.S. Pat. No. 4,601,797, Japanese patent J60100536, J60103193 and EP-A-189120), or carbonylation of secondary benzyl halides (J. Organometallic chemistry 282, (1985) 277-282, U.S. Pat. No. 4,536,595, EP Nos. 76721, 76722, or by the coupling of alpha-halopropionic acid with 2-(6-methoxynaphthyl) copper (U.S. Pat. No. 3,658,863), zinc (U.S. Pat. No. 3,663,584), cadmium (U.S. Pat. Nos. 3,658,858 and 3,694,476) or coupling of aryl magnesium halides with potassium 2-iodopropionate (German OLS No. 2145650) or reaction of aryl Grignard reagent with lithium, sodium, magnesium salts of 2-bromopropionic acids (U.S. Pat. No. 3,959,364) or carbonylation of aryl halide with CO and cobalt catalyst (U.S. Pat. No. 3,974,202), Palladium catalyst (U.S. Pat. No. 4,713,484) or by the arrangement of alpha-haloketals in the presence of a lewis acid (EP No. 0034871).

However, all above methods suffer from one or the other limitations like multistep synthesis, use of expensive and hazardous organometallic agents besides the problems in maintenance of high CO pressure.

In view of the above concerns, there have been continuing efforts to develop alternative synthetic approaches towards the immensely important 2-aryl alkanoic acid framework. In this context, the synthesis of 2-aryl alkanoic acids through the respective 2-aryl aldehydes as a useful synthon constitutes a simple and straight forward procedure which has been described in the prior art (C. Commun. 2007, 1739-1741, J. Org. Chem. 1999, 64, 5029-5035, Organometallics 10, 1183-1189 1991, WO 9303839).

In addition to their above usefulness as critical intermediates for the synthesis of commercially important anti-inflammatory drugs, the various other 2-aryl aldehyde analogues and especially the 2,2-diaryl aldehydes have recently been found to be privileged structural motifs for accessing some new potent anticancer compounds (U.S. Pat. No. 6,943,194 B1, J. Org. Chem. 1996, 65, 7438-7444). In particular, the above prior art discloses the formation of some novel trimethoxystilbene based benzophenone derivatives namely hydroxy phenstatin which showed potent inhibition of tubulin assembly ($IC_{50}$=0.82 µM) and exhibited an $ED_{50}$ of 0.25 µg/ml against the P388 lymphocytic leukemia cell lines, thus establishing their potent antitumor and antimitotic credentials. In the light of above discussion, it would be clear that a putative stilbene based benzophenone scaffold holds immense potential for displaying useful medicinal properties including anticancer activities. However, the synthesis of above medicinally important compounds themselves depend on the availability of critical synthons including the corresponding 2,2-diaryl aldehydes as evident in the prior art (U.S. Pat. No. 6,943,194 B1, J. Org. Chem. 1996, 65, 7438-7444). It is also evident that the various 2-aryl aldehydes and analogues such as 2,2-diaryl aldehydes constitute a privileged class of compounds with diverse applications for the synthesis of commercially and medicinally important compounds. However, the development of a convenient and economical protocol for the synthesis of above synthon i.e. 2-aryl aldehydes from easily available substrates like aryl alkenes has in itself remained tedious and expensive proposition. For instance, Organometallics 1991, 10, 1183-1189 discloses a method for multistep synthesis of 2-aryl aldehydes from the corresponding aryl ethenes utilizing expensive and hazardous reagents like rhodium catalyst and BINAPHOS ligand.

Similarly, J. Org. Chem. 1997, 62, 6547-6561 discloses a method for the formation of 2-aryl and 2,2-diaryl aldehydes via a multistep methodology involving the formation of epoxide from aryl alkene and its subsequent rearrangement using toxic palladium catalyst and phosphine ligands.

Similarly, J. Org. Chem. 1998, 63, 8212-8216 discloses a multistep method for the formation of 2-aryl and 2,2-diaryl aldehydes from respective aryl alkenes via the rearrangement of an intermediate epoxide using rare and expensive $InCl_3$ as a lewis acid.

In yet another instance, 2-aryl aldehydes were synthesized via the rearrangement of epoxides obtained from the corresponding aryl alkenes using lithium perchlorate as a lewis acid catalyst (J. Org. Chem. 1996, 61, 1877-1879).

Similarly, the 2-aryl and 2,2-diaryl aldehydes were synthesized via the rearrangement of corresponding epoxides using expensive $IrCl_3$ as a lewis acid catalyst (Tetrahedron Lett. 44, 2003, 7687-7689).

In a Similar manner, J. Org. Chem. 1996, 65, 7438-7444 discloses the multistep formation of 2,2-diaryl aldehydes from the corresponding stilbenes using boron trifluoride etherate catalyst.

In another instance, 2-aryl aldehydes were synthesized from the corresponding aryl alkenes, however, the methodology required an indispensable usage of base catalyst in the form of hazardous heavy metal salts like silver oxide etc. which precludes its use in case of substrates containing base sensitive groups. (Chem. lett. 1984, 341-344). In addition, the above methodology might also lead to production of corresponding carboxylic acids, as undesired side product, due to the known tendency of silver oxides for such a transformation (*Tetrahedron: Asymmetry*, 2005, 16, 1837-1843).

In view of the above, it is quite apparent that there has been a dearth of convenient protocols for the direct synthesis of 2-aryl aldehydes and analogues such as 2,2-diaryl aldehydes from corresponding arylalkenes as almost all the prevalent methods utilize multiple steps involving an intermediate epoxide besides the use of toxic, rare, and expensive transition metal/organometallic catalysts.

Thus, it becomes an object of the present invention to develop a convenient, economical and environment friendly synthetic methodology which not only provides the highly valuable 2-aryl and 2,2-diaryl aldehydes from the corresponding aryl alkenes in a single step but also simultaneously eliminates the hitherto indespensible requirement of expensive and hazardous transition metal catalysts.

OBJECTIVES OF THE INVENTION

The main object of the present invention is to provide a method for the microwave induced single step synthesis of novel 2-aryl aldehydes and analogues.

Another object of the present invention is to prepare some 2-aryl aldehydes which are commercially important synthons for the non steroidal anti-inflammatory drugs.

Yet another object of the present invention is to provide a process for the preparation of 2,2-diaryl aldehydes which are critical synthons for medicinally important compounds possessing potent anticancer activity.

Yet another object of the invention is to provide a process to prepare 2-aryl aldehydes and analogues from the corresponding aryl alkenes in a single step.

Yet another object of the invention is to provide a process to prepare 2-aryl aldehydes and analogues from the corresponding aryl alkenes without the use of any expensive and hazardous transition metal catalysts.

Yet another object of the invention is to provide a process to prepare 2-aryl aldehydes and analogues under environmentally safe aqueous conditions.

Yet another object of the invention is to provide a simple process for the preparation of 2-aryl aldehydes and analogues in high purity with minimum side products.

Yet another object of the invention is to provide a process wherein the ionic liquids used as solvents are recyclable.

Still another object of the invention is to provide a process which utilizes less hazardous or non-hazardous chemicals.

Yet another object of the invention is to develop industrially viable and economical process towards the formation of high valued 2-aryl aldehydes and analogues.

SUMMARY OF THE INVENTION

The present invention provides a process for the preparation of 2-aryl aldehydes and analogues which are critical intermediates both for the synthesis of commercially important anti-inflammatory drugs like naproxen and medicinally important potent anticancer compounds like phenstatin and many others in a single step under microwave irradiation by reaction of the corresponding aryl alkene with N-halosuccinimide in the presence of a phase transfer catalyst and solvent. N-halosuccinimide used is selected from the group consisting of N-bromosuccinimide, N-iodosuccinimide, N-chlorosuccinimide and the like. Solvent for the process is selected from a group consisting of dimethyl sulphoxide, dimethylformamide, dimethoxyethane, ionic liquids and the like. The final product i.e. 2-aryl aldehydes and analogues are obtained in good to moderate yields varying from 35-55% within 1 min-16 hrs depending upon the substrate and reagent mixture. It is worthwhile to mention that this microwave-assisted unique process in fact represents a novel, economical and environment friendly approach for the direct synthesis of highly valued 2-aryl aldehydes and analogues from corresponding aryl alkenes under aqueous conditions without the use of hitherto indispensable, expensive and hazardous transition metal catalysts.

Accordingly, the present invention provides novel 2-aryl aldehydes of the general formula 1:

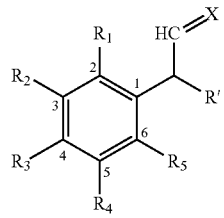

Formula 1 wherein, R' is selected from $CH_3$, $C_2H_5$, $C_6H_5$ or $C_6H_4$-(4'-$OCH_3$); X represents O or N—NH—$SO_2$—$C_6H_4$—$CH_3$; the substituents amongst $R_1$ to $R_5$ are selected from a group consisting of H, OH, $OCH_3$, $C_6H_5$, halogen atom or $R_2+R_3$ together represent (CH=CH—CH=CH) group or (O—$CH_2$—O) group and $R_1$, $R_4$, $R_5$ are selected from a group consisting of H, OH, $OCH_3$, $C_6H_5$, halogen atom;

In another embodiment of the present invention, the representative compounds of the general formula 1 comprising:
(i) 2-(2,4,5 trimethoxy phenyl)propionaldehyde;
(ii) 2-(2,4,5 trimethoxy phenyl)propionaldehyde tosyl hydrazone;
(iii) 2-(1-naphthyl)-butylaldehyde;
(iv) 2-(2-bromo-3,4-dimethoxyphenyl)propionaldehyde;
(v) 2-(2-bromo-3,4-dimethoxyphenyl)propionaldehyde tosyl hydrazone;
(vi) 2-(4-hydroxy, 3-methoxyphenyl)-2-(4'-methoxyphenyl)acetaldehyde.

In yet another embodiment of the present invention, a microwave induced single step synthesis of 2-aryl aldehydes and analogues of general formula 1, wherein the said process comprising the steps of:
a) reacting substituted aryl alkene and N-halosuccinimide and a phase transfer catalyst in a solvent under conventional or microwave irradiation;
b) transferring the reaction mixture of step (a) into ice cold water and extracting with an organic solvent;
c) washing the organic solution of step (b) with aqueous sodium thiosuphate, brine and water,
d) drying the organic layer of step (c) over anhydrous sodium sulphate, filtering and evaporating to dryness to completely remove the solvent to obtain a residue,
e) purifying the residue of step (d) on Si-gel (60-120 mesh size) with a 1:10 to 4:6 mixture of ethylacetate and hexane to obtain the required substituted 2-aryl aldehydes of general formula 1.

In yet another embodiment of the present invention, the N-halosuccinimide used is selected from the group consisting of N-bromosuccinimide, N-iodosuccinimide, N-chlorosuccinimide or a combination thereof.

In still another embodiment of the present invention, the solvent used in step (a) is either water or a mixture of water-organic solvent wherein the organic solvent is selected from the group consisting of dimethyl sulphoxide, dioxane, dimethylformamide, dimethoxyethane, ionic liquids or a combination thereof.

In still another embodiment of the present invention, the phase transfer catalyst is selected from a group consisting of CTAB, CTAC or various chiral phase transfer catalysts such as N-benzylcinchonidinium chloride.

In still another embodiment of the present invention, the developed process is applied equally successfully on aromatic ring in aryl alkenes.

In yet another embodiment the organic solvent used in step (b) is ethyl acetate.

In yet another embodiment of the present invention, the claimed process is found workable in both a monomode and a multimode microwave.

In yet another embodiment of the present invention, the reaction is performed in a monomode microwave organic synthesizer operated at 50-300 W power level with 120-200° C. for 1-45 min, irradiation frequency used is in the range of 900 to 3000 MHz, more preferably in the range of 2450 to 2455 MHz.

In furthure another embodiment of the present invention, the mole ratio between substituted arylalkene and N-halosuccinimide is ranging between 1:1 to 1:3 moles.

In still furthure another embodiment of the present invention, the volume ratio of water and organic solvent is in the range of 1:4 to 4:1, preferably being 3:1.

In still another embodiment of the present invention, the mole ratio between the substituted arylalkene and phase transfer catalyst is ranging between 1:0.1 to 1:0.5 moles.

In still yet another embodiment of the present invention, halohydrin formation and subsequent rearrangement to 2-aryl aldehydes from corresponding aryl alkanols occur in the same pot without the formation of an intermediate epoxide or use of a transition metal catalyst, lewis acid/base.

In still yet another embodiment of the present invention, the claimed process can be used for the preparation of 2-aryl aldehydes, 2,2-diaryl aldehydes and analogues which are important intermediates for commercially important nonsteroidal anti-inflammatory drugs and some medicinally important potent anticancer compounds by taking different substrates.

In still another embodiment of the present invention, the use of chiral phase transfer catalyst provides asymmetric access towards chiral 2-aryl aldehyde.

DETAILED DESCRIPTION OF THE INVENTION

Figure 1:
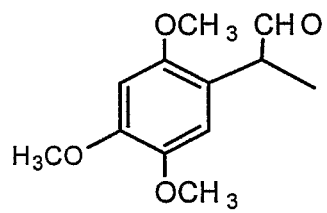
FIG. 1 2-(2,4,5 trimethoxyphenyl)propionaldehyde
FIG. 2 2-(2,4,5 trimethoxyphenyl) propionaldehyde tosyl hydrazone
FIG. 3 2-(1-naphthyl)propionaldehyde
FIG. 4 2-(1-naphthyl)butylaldehyde
FIG. 5 2-(6-methoxy-2-naphthyl)propionaldehyde
FIG. 6 2-(3,4-dioxymethylene phenyl)propionaldehyde
FIG. 7a 2-(2-bromo-3,4-dimethoxyphenyl)propionaldehyde tosyl hydrazone
FIG. 7b 2-(2-bromo-3,4-dimethoxyphenyl)propionaldehyde
FIG. 8 2-(4-methoxyphenyl)propionaldehyde
FIG. 9 2-(4-hydroxy, 3-methoxyphenyl)-2-(4'-methoxyphenyl) acetaldehyde

In the context of above discussion, it would be quite apparent that the 2-aryl aldehydes and analogues represent a class of immensely important compounds finding applications as critical synthons for a diverse range of commercially and medicinally important molecules. However, the development of an economical and ecofriendly synthetic methodology for above 2-aryl aldehydes and analogues from easily available aryl alkenes has been a difficult proposition as almost all prevalent methodologies involve multistep transformations utilizing rare, expensive and environmentally hazardous transition metal catalysts. It, therefore, becomes an object of the invention to provide a single step and economical process for the preparation of some novel 2-aryl aldehydes and analogues from cheap and commercially available substituted arylalkenes as well as to eliminate the disadvantages associated with the above patents and papers. It is worthwhile to mention that microwave-assisted (A. K. Bose, B. K. Banik, N. Lavlinskaia, M. Jayaraman, M. S. Manhas, *Chemtech,* 1997, 27, 18; M. Larhed, Hallberg, *Drug Discovery Today,* 2001, 6(8), 406) chemical transformation has been widely recognized to provide ecofriendly, rapid and high yielding process. However, the present invention embodies a unique instance wherein microwave irradiation induces a single step conversion of arylalkenes to corresponding 2-aryl aldehydes in environmentally safe aqueous conditions without the use of any transition metal catalysts.

Thus, we disclose a unique and economical process to prepare 2-aryl aldehydes and their analogues in a single step from the respective substituted arylalkenes, N-halosuccinimide in the presence of a phase transfer catalyst, and solvent. In fact, the present invention is the result of an unexpected albeit delightful finding, wherein in the course of our efforts to utilize the abundantly available β-asarone rich *Acorus calamus* oil for synthesis of some natural products, we undertook the addition of N-bromosuccinimide to beta-asarone in DMSO-Water solvent mixture under microwave irradiation. However, to our surprise in addition to the expected bromohydrin the reaction provided traces of the corresponding 2-aryl aldehyde. The above finding attracted our attention and we were able to optimize the reaction conditions using combinations of solvents and phase transfer catalysts to provide the 2-aryl aldehyde product in moderate to good yield. The compound was analyzed on the basis of its spectral data ($^1$H and $^{13}$C NMR) and found to be a novel 2-aryl aldehyde (Example I). Subsequently, the same method was applied to other substituted aryl alkenes and upon reaction with NBS, the desired 2-aryl aldehydes were successfully obtained. Interestingly, the above reaction was also found to be feasible in neat water i.e without the addition of any organic solvent though the yield was comparatively lower in this case. It is pertinent to mention that in the case of 3,4 substituted phenyl alkenes like methylisoeugenol and isosaffrole, the above reaction was found to provide a mixture of desired 2-aryl aldehyde and an unexpected orthobrominated 2-arylaldehyde.

However, a decrease in amount of NBS (1 mmol in place of 2 mmol.) was found to be sufficient to provide the corresponding 2-arylaldehyde as a single product. Consequent to the above success with phenylalkenes, we ventured to extend the developed method towards a metal/base free synthesis of 6-methoxy-2-naphthyl propionaldehyde which is an important precursor of commercial anti-inflammatory drug naproxen. However, the corresponding 6-methoxy-2-naphthyl propene was found to be insoluble in the developed solvent system comprising Water-DMSO in 3:1 ratio. The variation of Water-DMSO ratio from 3:1 to 1:3 was also found to be of no avail, however, a Dioxane:Water (3:1) combination in was found to provide the required 6-methoxy-2-naphthyl propionaldehyde in 15% yield after 45 min of MW. In order to further enhance the above reaction performance, we decided to conduct the above reaction by replacing NBS with NIS and the yield was found to increase upto 60% after 20 min of MW. The above reagent system comprising of NIS and Dioxane:Water (3:1 ratio) was also found to be optimum in the course of our efforts towards extending the developed method for synthesis of various 2,2-diarylaldehydes as 4-hydroxy-3,4'-dimethoxystilbene also provided the corresponding 2,2-diaryl aldehydes in 51% yield respectively.

It may be mentioned that developed single step methodology was also attempted under ultrasonication or a heating mantel instead of microwave conditions (Example IV). However, the desired 2-aryl aldehyde was obtained in very low yield and long reaction times along with several side products. The above finding emphatically shows the critical role of microwave in selectively providing the desired product in good yield and short reaction time.

In addition to the conversion of arylalkenes to corresponding 2-arylaldehydes, the above methodology was also extended towards a direct conversion of aryl alkanols to aryl aldehydes wherein, the arylakanol is dehydrated with DMSO or ionic liquid and subsequently treated with NBS to obtain the required 2-arylaldehydes. Evidently, the above three step sequence further widens the scope of developed method towards widely available substrates like arylalkanols/arylalkenes.

In conclusion, our invention discloses a simple and economical process for preparing various 2-aryl aldehydes and analogues which are critical intermediates for several commercially and medicinally important compounds. The method utilizes relatively cheap and economical material in the form of substituted arylalkenes, reagents such as N-halosuccinimide and a solvent under microwave or conventional conditions. The developed process provides a novel and economical single step synthetic methodology for accessing various 2-aryl and 2,2-diaryl aldehydes under environmentally friendly aqueous conditions without the use of hitherto indispensable expensive transition metal catalysts.

The following examples are given by way of illustration and therefore should not be construed to limit the scope of the present invention.

EXAMPLE I

Synthesis of 2-(2,4,5 trimethoxy phenyl)propionaldehyde (from formula I where $R_1$, $R_3$, $R_4$=OMe, $R_2$, $R_5$=H, R'=$CH_3$ and X=O): FIG. 1

A mixture of 2,4,5 trimethoxy phenyl propene (1 mmol), N-bromosuccinimide (1.5 mmol), water (12 ml), DMSO (3 ml), cetyltrimethyl ammonium bromide (0.3 mmol) were taken in a 100 ml round bottom flask fitted with a condenser. The flask was shaken well and placed inside the monomode microwave oven and irradiated (220 W, 200° C.) for 12 minutes in parts. The cooled mixture was poured into ice-cold water and extracted with ethyl acetate. The organic layer was washed with aq. sodium thiosulphate, brine and then organic layer dried over anhydrous sodium sulphate. The solvent was evaporated under reduced pressure to obtain a liquid which was purified on silica gel by column chromatography using a mixture of hexane and ethyl acetate (9:1 to 6:4), provided white viscous liquid; 60% yield; $^1$H NMR (CDCl$_3$) δ 9.56 (1H, s), 6.55 (1H,s), 6.49 (1H, s), 3.82 (3H, s), 3.75 (3H, s), 3.73 (3H, s); d$_C$ (75.4 MHz, CDCl$_3$) 201.9, 151.5, 149.1, 143.3, 118.0, 113.7, 113.0, 111.1, 97.7, 56.7, 56.3, 56.2 and 46.8. Mass (M+1) calculated 225.2645, observed 225.2642.

EXAMPLE II

Figure 2:
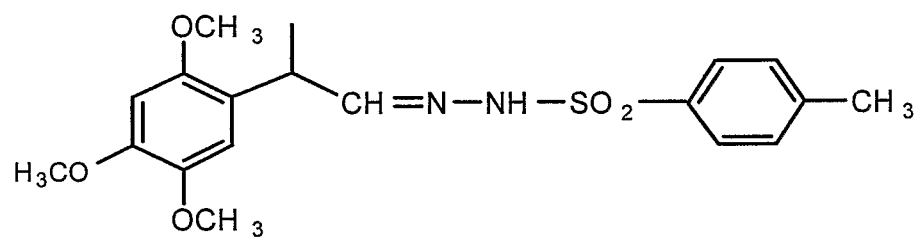

Synthesis of 2-(2,4,5 trimethoxy phenyl)propionaldehyde tosyl hydrazone (from formula I where $R_1$, $R_3$, $R_4$=OMe, $R_2$, $R_5$=H, R'=$CH_3$ and X=N—NH—SO$_2$—C$_6$H$_4$—CH$_3$) FIG. 2

The structure of above obtained 2-(2,4,5 trimethoxy phenyl)propionaldehyde (example 1) was further confirmed when the treatment of above aldehyde (1 mmol) with p-toluenesulphonyl hydrazide (1 mmol) in methanol as a solvent provided the corresponding hydrazone derivative (2-(2,4,5 trimethoxy phenyl)propionaldehyde tosyl hydrazone) in 60% yield; white solid m.p (150-151° C.), $^1$H NMR (CDCl$_3$) δ 9.63 (1H, s), 7.79 (2H, d), 7.42 (2H, d), 6.67 (1H, s), 6.50 (1H, s), 3.92 (1H, q), 3.85 (3H, s), 3.74 (3H, s), 3.61 (3H, s), 2.38 (3H, s), 1.2 (3H, d) d$_C$ (75.4 MHz, CDCl$_3$) 154.6, 152.0, 149.8, 144.2-137.3, 130.0, 128.4, 122.4, 113.9, 99.5, 56.9, 56.6, 56.2, 36.3, 21.2 and 17.6.

EXAMPLE III

Synthesis of 2-(2,4,5 trimethoxy phenyl)propionaldehyde (from formula I where $R_1$, $R_3$, $R_4$=OMe, $R_2$, $R_5$=H, R'=$CH_3$ and X=O): FIG. 1

A mixture of 2,4,5 trimethoxy phenyl propene (1 mmol), N-bromosuccinimide (1.5 mmol), water (12 ml), DMSO (3 ml), cetyltrimethyl ammonium bromide (0.3 mmol) was taken in a 100 ml Erlenmeyer flask fitted with loose funnel at the top. The flask was shaken well and placed inside the multimode microwave oven and irradiated (900 W) for 8 minutes in parts. After completion of reaction, the reaction mixture was worked up as in example-1 to provide the corresponding 2-(2,4,5 trimethoxy phenyl)propionaldehyde (45% yield) whose spectral data matched with that mentioned in example-1.

EXAMPLE IV

Synthesis of 2-(2,4,5 trimethoxy phenyl)propionaldehyde (from formula I where $R_1$, $R_3$, $R_4$=OMe, $R_2$, $R_5$=H, R'=$CH_3$ and X=O): FIG. 1

A mixture of 2,4,5 trimethoxy phenyl propene (1 mmol), N-bromosuccinimide (1.2 mmol), water (14 ml), cetyltrimethyl ammonium bromide (0.3 mmol) were taken in a 100 ml round bottom flask fitted with a condenser. The flask was shaken well and placed inside the monomode microwave oven and irradiated (220 W, 200° C.) for 12 minutes in parts. After completion of reaction, the reaction mixture was worked up as in example-1 to provide the corresponding 2-(2,4,5 trimethoxy phenyl)propionaldehyde (43% yield) whose spectral data matched with that mentioned in example-1.

EXAMPLE V

Figure 3:
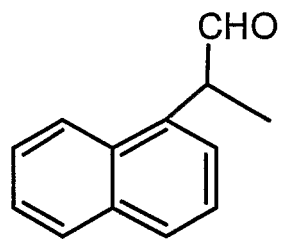

Synthesis of 2-(1-naphthyl)-propionaldehyde (from formula I where $R_2$+$R_3$=(CH=CH—CH=CH), R1, R4, R5=H, R'=$CH_3$ and X=O): FIG. 3

A mixture of 1-(1-Naphthyl)-prop-1-ene (1.2 mmol), N-Bromosuccinimide (2 mmol), water (12 ml), DMSO (3 ml), cetyltrimethyl ammonium bromide (0.28 mmol) were taken in a 100 ml round bottom flask fitted with a condenser. The flask was shaken well and placed inside the monomode microwave oven and irradiated (220 W, 200° C.) for 12 minutes in parts. The cooled mixture was poured into ice-cold water and extracted with ethyl acetate. The organic layer was washed with aq. sodium thiosulphate, brine and then organic layer dried over sodium sulphate. The solvent was evaporated under reduced pressure to obtain a liquid which was purified on silica gel by column chromatography, using a mixture of hexane and ethyl acetate (9:1 to 6:4), provided a white viscous liquid; 50% yield; $^1$H NMR (CDCl$_3$, 300 MHz) 9.69 (1H, s), 7.97 (1H, d), 7.86 (1H, d), 7.78 (1H, d), 7.53 (3H, m), 7.2 (1H d), 4.36 (1H,q), 1.53 (3H, d): d$_C$ (75.4 MHz, CDCl$_3$) 201.3, 134.1, 129.1, 128.3, 126.7, 126.0, 125.6, 124.9, 122.3, 48.8 and 14.6.

EXAMPLE VI

Figure 4:
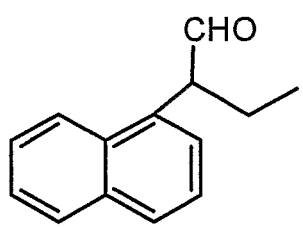

Synthesis of 2-(1-naphthyl)-butylaldehyde (from formula I where R$_2$+R$_3$=(CH=CH—CH=CH), R1, R4, R5=H and R'=CH$_2$—CH$_3$ and X=O): FIG. 4

A mixture of 1-(1-Naphthyl)-But-1-ene (1.2 mmol), N-Iodosuccinimide (1.5 mmol), water (3 ml), Dioxane (12 ml), cetyltrimethyl ammonium bromide (0.28 mmol) were taken in a 100 ml round bottom flask fitted with a condenser. The flask was shaken well and placed inside the monomode microwave oven and irradiated (150 W, 120° C.) for 12 minutes in parts. The cooled mixture was poured into ice-cold water and extracted with ethyl acetate. The organic layer was washed with aq. sodium thiosulphate, brine and then organic layer dried over sodium sulphate. The solvent was evaporated under reduced pressure to obtain a liquid which was purified on silica gel by column chromatography, using a mixture of hexane and ethyl acetate (9:1 to 6:4), to provide a white viscous liquid; 70% yield; $^1$H NMR (CDCl$_3$, 300 MHz) 9.68 (1H, d), 8.03 (1H, s), 7.88 (1H, d), 7.81 (1H, d), 7.53-7.43 (3H, m), 7.29 (1H, d), 4.16-4.15 (1H, m), 2.30-2.25 (1H, m), 1.93-1.88 (1H, m), 0.97 (3H, t): d$_C$ (75.4 MHz, CDCl$_3$) 200.9, 134.3, 132.7, 132.3, 129.2, 128.3, 126.7, 126.2, 126.0, 125.6, 123.2, 56.3, 22.9 and 12.1. HRMS (M+1) calculated 199.27294, observed 199.2726.

EXAMPLE VII

Figure 5:
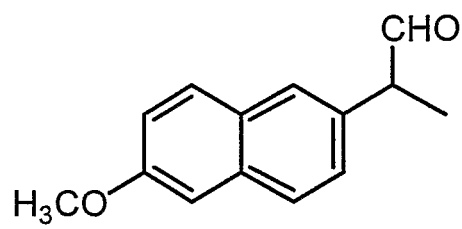

Synthesis of 2-(6-methoxy-2-naphthyl)-propionaldehyde (from formula I where R$_2$+R$_3$=(CH=CH—CH=CH), R$_5$=OCH$_3$, R$_1$, R$_4$, R$_5$=H, R'=CH$_3$ and X=O): FIG. 5

A mixture of 1-(6-methoxy-2-Naphthyl)-prop-1-ene (1.2 mmol), N-iodosuccinimide (2 mmol), water (3 ml), Dioxane (11 ml), cetyltrimethyl ammonium bromide (0.28 mmol) were taken in a 100 ml round bottom flask fitted with a condenser. The flask was shaken well and placed inside the monomode microwave oven and irradiated (220 W, 200° C.) for 12 minutes in parts. The cooled mixture was poured into ice-cold water and extracted with ethyl acetate. The organic layer was washed with aq. sodium thiosulphate, brine and then organic layer dried over sodium sulphate. The solvent was evaporated under reduced pressure to obtain a liquid which was purified on silica gel by column chromatography, using a mixture of hexane and ethyl acetate (9:1 to 6:4), provided a white viscous liquid; 55% yield; $^1$H NMR (CDCl$_3$, 300 MHz) 9.83 (1H, s), 7.85-7.79 (3H, t), 7.68 (1H, s), 5.70 (1H, s), 7.38-7.34 (1H, m), 7.28-7.22 (1H, m), 3.99 (3H, s), 3.85 (1H, q), 1.62 (3H d); d$_C$ (75.4 MHz, CDCl$_3$), 201.2, 158.0, 136.2, 132.8, 129.3, 127.8, 127.5, 127.1, 119.4, 105.7, 55.4, 53.0 and 17.6.

EXAMPLE VIII

Figure 6:
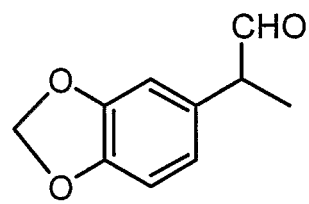

Synthesis of 2-(3,4-dioxymethylene phenyl)propionaldehyde (from formula I where R$_2$+R$_3$=O—CH$_2$—O, R'=CH$_3$, R$_1$, R$_4$, R$_5$=H and X=O): FIG. 6

A mixture of isosaffrole (1.2 mmol), N-bromosuccinimide (1.2 mmol), water (12 ml), DMSO (3 ml), cetyltrimethyl ammonium bromide (0.28 mmol) were taken in a 100 ml round bottom flask fitted with a condenser. The flask was shaken well and placed inside the monomode microwave oven and irradiated (220 W, 200° C.) for 12 minutes in parts. The cooled mixture was poured into ice-cold water and extracted with ethyl acetate. The organic layer was washed with aq. sodium thiosulphate, brine and then organic layer dried over sodium sulphate. The solvent was evaporated under reduced pressure to obtain a liquid which was purified on silica gel by column chromatography using a mixture of hexane and ethyl acetate (9:1 to 6:4), provided a white viscous liquid; 42% yield; $^1$H NMR (CDCl$_3$ 300 MHz), 9.55 (1H, s), 6.75 (1H,d), 6.60-6.57 (2H, m), 5.90 (2H, s), 3.5 (1H,q), 1.3 (3H, m): d$_C$ (75.4 MHz, CDCl$_3$) 201.0, 148.4, 147.2, 131.5, 121.7, 108.9, 108.7, 101.3, 52.7 and 14.8.

EXAMPLE IX

Figure 7A:
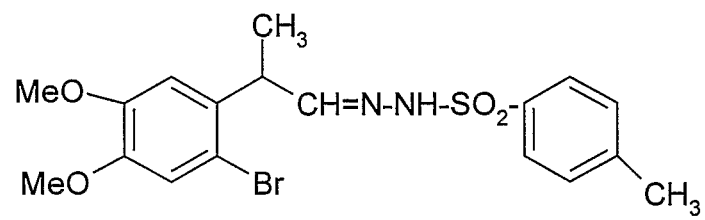
Figure 7B:
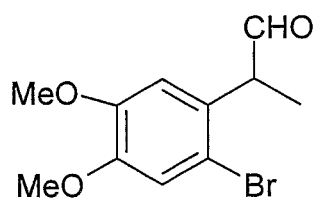

Synthesis of 2-(2-bromo-3,4-dimethoxyphenyl)propionaldehyde (from formula I where R$_1$=Br, R$_2$, R$_3$=OMe, R'=CH$_3$, R$_4$, R$_5$=H and X=O): FIG. 7b A mixture of methylisoeugenol (1.2 mmol), N-bromosuccinimide (3 mmol), water (12 ml), DMSO (3 ml), cetyltrimethyl ammonium bromide (0.28 mmol) were taken in a 100 ml round bottom flask fitted with a condenser. The flask was shaken well and placed inside the monomode microwave oven and irradiated (220 W, 200° C.) for 12 minutes in parts. The cooled mixture was poured into ice-cold water and extracted with ethyl acetate. The organic layer was washed with aq. sodium thiosulphate, brine and then organic layer dried over sodium sulphate. The solvent was evaporated under reduced pressure to obtain a liquid which was purified on silica gel by column chromatography using a mixture of hexane and ethyl acetate (9:1 to 6:4), provided a white viscous liquid; 70% yield; $^1$H NMR (CDCl$_3$ 300 MHz) 9.63 (1H, s), 7.02 (1H, s) 6.48 (1H, s), 4.06 (1H, q), 3.80 (3H, s), 3.77 (3H, s), 1.36 (3H, d): d$_C$ (75.4 MHz, CDCl$_3$) 200.6, 149.2, 129.5, 116.1, 115.2, 111.6, 56.38, 56.31, 51.8 and 14.1.

The above obtained brominated aryl aldehyde was further dehalogenated to provide the corresponding product i.e. 2-(3, 4-dimethoxyphenyl)propionaldehyde; $^1$H NMR (CDCl$_3$ 300 MHz) 9.57 (1H, s), 6.81 (1H, d) 6.70 (1H, d), 6.61 (1H, s), 3.80 (6H, s), 1.36 (3H, d): d$_C$ (75.4 MHz, CDCl$_3$) 201.0, 149.4, 148.5, 130.0, 120.4, 111.6, 111.3, 55.90, 52.50 and 14.6.

EXAMPLE X

Synthesis of 2-(2-bromo-3,4-dimethoxyphenyl)propionaldehyde tosyl hydrazone (from formula I where R$_1$=Br, R$_2$, R$_3$=OMe, R'=CH$_3$ and X=tosyl hydrazone): FIG. 7a The structure of above obtained 2-(2-bromo-3,4-dimethoxyphenyl)propionaldehyde was further confirmed when the treatment of above aldehyde (1 mmol) with p-toluenesulphonyl hydrazide (1 mmol) in methanol as a solvent provided the corresponding hydrazone derivative 2-(2-bromo-3,4-dimethoxyphenyl)propionaldehyde tosyl hydrazone $^1$H NMR (CDCl$_3$) δ 8.06 (1H, s), 7.82 (2H, d), 7.31 (2H, d), 7.21-7.18 (1H, m), 6.74 (1H, d), 6.62 (1H, d), 6.60 (1H, s), 3.87 (3H, s), 3.73 (3H, s), 3.61-3.53 (1H, 1q), 2.44 (3H, s), 1.37 (3H, d) d$_C$ (75.4 MHz, CDCl$_3$) 153.2, 149.2, 149.0, 144.1-135.2, 132.8, 129.5, 128.1, 115.6, 114.06, 111.08, 56.2, 55.9, 41.5, 21.6 and 15.3.

EXAMPLE XI

Figure 8:
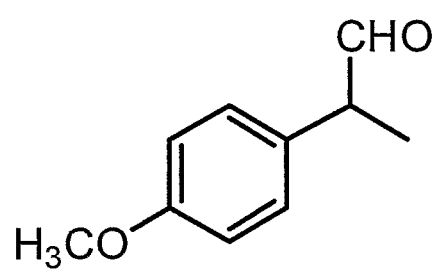

Synthesis of 2-(4-methoxy phenyl)propionaldehyde (from formula I where R$_3$=OCH$_3$, R$_1$, R$_2$, R$_4$, R$_5$=H, R'=CH$_3$ and X=O): FIG. 8

A mixture of anethole (1.2 mmol), N-bromosuccinimide (1.8 mmol), water (12 ml), DMSO (3 ml), cetyltrimethyl ammonium bromide (0.28 mmol) were taken in a 100 ml round bottom flask fitted with a condenser. The flask was shaken well and placed inside the monomode microwave oven and irradiated (220 W, 200° C.) for 12 minutes in parts. The cooled mixture was poured into ice-cold water and extracted with ethyl acetate. The organic layer was washed with aq. sodium thiosulphate, brine and then organic layer dried over sodium sulphate. The solvent was evaporated under reduced pressure to obtain a liquid which was purified on silica gel by column chromatography using a mixture of hexane and ethyl acetate (9:1 to 6:4), provided a white viscous liquid; 65% yield; $^1$H NMR (CDCl$_3$, 300 MHz), 9.58 (1H, s), 7.07 (2H, d), 6.86 (2H, d), 3.74 (3H, s), 1.36 (3H, d); $^{13}$C NMR (CDCl$_3$, 75.4 MHz) 201.2, 159.0, 129.6, 123.7, 55.3, 52.1 and 29.7.

EXAMPLE XII

Figure 9:
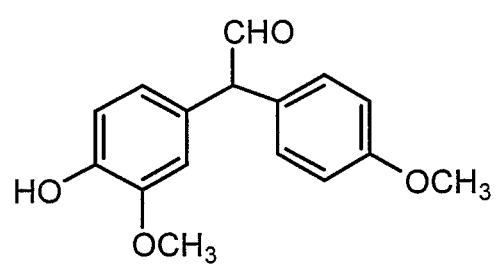

Synthesis of 2-(4-hydroxy, 3-methoxyphenyl)-2-(4'-methoxyphenyl)acetaldehyde (from formula I where R$_1$, R$_2$, R$_5$=H, R$_3$=OH, R$_4$=OMe, R'=Ph-(4'-OMe) and X=O: FIG. 9

A mixture of 4-hydroxy-3,4'-dimethoxy stilbene (0.8 mmol), N-Iodosuccinimide (1.6 mmol), water (3 ml), Dioxane (12 ml), cetyltrimethyl ammonium bromide (0.3 mmol) were taken in a 100 ml round bottom flask fitted with a condenser. The flask was shaken well and placed inside the monomode microwave oven and irradiated (150 W, 120° C.) for 12 minutes in parts. The cooled mixture was poured into ice-cold water and extracted with ethyl acetate. The organic layer was washed with aq. sodium thiosulphate, brine and then organic layer dried over sodium sulphate. The solvent was evaporated under reduced pressure to obtain a liquid which was purified on silica gel by column chromatography using a mixture of hexane and ethyl acetate (9:1 to 6:4), provided a white viscous liquid; 51% yield; $^1$H NMR (CDCl$_3$, 300 MHz) 9.79 (1H, s), 7.18 (2H, d), 6.70-6.90 (5H, m), 5.70 (1H, s), 3.84 (3H, s), 3.82 (3H, s); d$_C$ (75.4 MHz, CDCl$_3$), 198.4, 159.6, 146.9, 145.8, 131.4, 131.1, 128.8, 120.7, 114.3, 114.2, 110.9, 82.9, 56.0 and 55.3. HRMS (M+1) calculated 273.3085, observed 273.3086.

EXAMPLE XIII

Synthesis of 2-(4-methoxy phenyl)propionaldehyde from corresponding aryl alkanol (Through One Pot Dehydration-Bromohydrin Formation-Rearrangement Sequence)

(from formula I where R$_1$, R$_2$, R$_4$, R$_5$=H, R$_3$=OCH$_3$ R'=CH$_3$ and X=O): FIG. 8

A mixture of 1-(4-methoxy-phenyl)-1-propanol (1.2 mmol), DMSO (3 ml) or [hmim] [Br](1.5 ml) were taken in a 100 ml round bottom flask fitted with a condenser. The flask was shaken well and placed inside the monomode microwave oven and irradiated (190 W, 170° C.) for 10 minutes in parts. To the above reaction mixture, N-bromosuccinimide (1.8 mmol), water (12 ml), cetyltrimethyl ammonium bromide (0.28 mmol) were added and irradiated under microwave (220 W, 200° C.) for 12 minutes in parts. The cooled mixture was poured into ice-cold water and extracted with ethyl acetate. The organic layer was washed with aq. sodium thiosulphate, brine and then organic layer dried over sodium sulphate. The solvent was evaporated under reduced pressure to obtain a liquid which was purified on silica gel by column chromatography using a mixture of hexane and ethyl acetate (9:1 to 6:4), provided a white viscous liquid; 50% yield; $^1$H NMR (CDCl$_3$, 300 MHz), 9.58 (1H, s), 7.07 (2H, d), 6.86 (2H, d), 3.74 (3H, s), 1.36 (3H, d); $^{13}$C NMR (CDCl$_3$, 75.4 MHz) 201.2, 159.0, 129.6, 123.7, 55.3, 52.1 and 29.7.

EXAMPLE XIV

Synthesis of 2-(3,4-dioxymethylene phenyl)propionaldehyde (using chiral N-benzyl cinchonidinium bromide)

(from formula I where R$_2$+R$_3$=O—CH$_2$—O, R'=CH$_3$, R$_1$, R$_2$, R$_5$=H and X=O): FIG. 6

A mixture of isosaffrole (1.2 mmol), N-bromosuccinimide (1.6 mmol), water (12 ml), DMSO (3 ml), N-benzyl cinchonidinium bromide (40 mol %) were taken in a 100 ml round bottom flask fitted with a condenser. The flask was shaken well and placed inside the monomode microwave oven and irradiated (250 W, 115° C.) for 15 minutes in parts. The cooled mixture was poured into ice-cold water and extracted with ethyl acetate. The organic layer was washed with aq. sodium thiosulphate, brine and then organic layer dried over sodium sulphate. The solvent was evaporated under reduced pressure to obtain a liquid which was purified on silica gel by column chromatography using a mixture of hexane and ethyl acetate (9:1 to 6:4), provided a colorless viscous liquid; (48% yield) whose spectral data matched well with that obtained in Example-VIII. The enantiomeric excess of above product was determined to be 30% on the basis of $^1$H NMR assay using L-valine methyl ester hydrocholoride as a chiral derivatizing agent.

The main advantages of the present invention are:
1. The main advantage of the present invention is to provide a microwave-assisted process for the preparation of novel 2-aryl and 2,2-diarylaldehydes including some commercially important analogues from substituted arylalkenes in a single step.
2. A process to prepare 2-arylaldehydes under environmentally friendly aqueous conditions.

3. A process for the preparation of 2-arylaldehydes in high purity with minimum or no side products.
4. A process wherein the ionic liquids used as solvent are recyclable.
5. An economical and industrial viable process for the preparation of high valued 2-arylaldehydes.

We claim:
1. A compound selected from the group consisting of:
2-(2,4,5 trimethoxy phenyl)propionaldehyde;
2-(2,4,5 trimethoxy phenyl)propionaldehyde tosyl hydrazone;
2-(1-naphthyl)-butylaldehyde;
2-(2-bromo-3,4-dimethoxyphenyl)propionaldehyde;
2-(2-bromo-3,4-dimethoxyphenyl)propionaldehyde tosyl hydrazone; and
2-(4-hydroxy, 3-methoxyphenyl)-2-(4'-methoxyphenyl)acetaldehyde.

* * * * *